United States Patent [19]
Rosenberg

[11] Patent Number: 5,316,475
[45] Date of Patent: May 31, 1994

[54] DENTAL PROPHY CUP

[76] Inventor: Neil A. Rosenberg, 32 Equator Dr., Nantucket, Mass. 02554

[21] Appl. No.: 14,249

[22] Filed: Feb. 5, 1993

[51] Int. Cl.⁵ ............................................. A61C 3/06
[52] U.S. Cl. ................................................ 433/166
[58] Field of Search .............................. 433/166, 125

[56] References Cited

U.S. PATENT DOCUMENTS

| | | | |
|---|---|---|---|
| 2,789,352 | 4/1957 | Wiseman | 433/166 |
| 3,472,045 | 10/1969 | Nelsen et al. | 433/166 |
| 3,478,433 | 11/1969 | Richmond | 433/125 |
| 4,259,071 | 3/1981 | Warden et al. | 433/166 |
| 5,083,922 | 1/1992 | Yale | 433/166 |

FOREIGN PATENT DOCUMENTS 376969 7/1932 United Kingdom ................ 433/166

Primary Examiner—John J. Wilson
Attorney, Agent, or Firm—Burns, Doane, Swecker & Mathis

[57] ABSTRACT

A dental prophy cup includes an elastically flexible rim which includes a flexure region of reduced thickness. The rim thickness increases to a region of maximum thickness at a location forwardly of the flexure region and then tapers downwardly toward a front end of the rim. A forwardly facing surface of the cup which contacts the tooth surface comprises two convex surface portions joined by a radiused bridge surface portion located at the flexure region. Abrasive particles are distributed within the body of the cup and are released as the base material of the cup breaks down.

17 Claims, 2 Drawing Sheets

DENTAL PROPHY CUP

BACKGROUND OF THE INVENTION

The present invention relates to a dental prophy cup used in dental prophylaxis procedures and, in particular, to a novel configuration and construction of such a cup.

A dental prophylaxis procedure typically involves the application of an abrasive paste (i.e., a paste containing abrasive particles) to a tooth surface upon which pressure and rotational motion are applied. The removal of plaque, calculus and stains is facilitated by the resultant abrasion at the interface between the abrasive particles and tooth surface.

The pressure and rotational motion are applied to the abrasive paste by means of a prophy cup which comprises a cup-shaped element of about one-quarter inch diameter, the outer peripheral wall of which is elastically flexible. The cup is mounted on a drive shaft which rotates the cup at high speed, e.g., about 1,500 rpm. An operator presses the cup against a tooth following the insertion of abrasive paste into the cup. The paste serves as a lubricant, and the abrasives in the paste function to abrade away plaque, calculus, and stains from the tooth surfaces.

This procedure has traditionally exhibited certain shortcomings. For example, during the prophylaxis procedure, the paste becomes diluted when coming into contact with saliva, blood and/or water. Since the amount of paste contained in the cup is small, e.g., about 0.1 gram, even a slight dilution has a pronounced adverse effect on the concentration of abrasive particles. As dilution increases, abrasion and performance decreases.

Additionally, the centrifugal force generated by a prophy cup rotating at 1,500 rpm causes the paste to be displaced in a radial direction. The amount of paste retained at the interface of the cup and tooth surface after one second (25 rotations) is a small fraction of the initial volume. The decreased amount of paste results in reduced abrasion and performance.

The above-described shortcomings involve a reduced availability of abrasive at the working area. Additional shortcomings, however, relate to the geometry of the cup. In that regard, prophy cups are designed to be flexible. That is, as the operator presses the cup against a tooth surface, the outer annular rim of the cup is intended to flex outwardly in order to increase the area of surface contact between the cup and the tooth. The present inventor has determined, however, that the amount of flexing exhibited by presently used cups results in a relatively narrow area of surface contact being established. That area is ring-shaped and less than 0.02 inch wide. This makes it difficult for the operator to control the magnitude and placement of abrasion.

If the cup rim were made thinner in order to increase its flexibility, then the outer portion of the rim may apply only weak forces to the abrasive particles, whereby the cleaning action is ineffective.

In one reported clinical test involving seventy-six patients, it was observed that following a prophylaxis cleaning procedure with conventional prophy cups, deposits remained on interproximal surfaces of all test teeth and on facial surfaces of over half the test teeth.

It would be desirable to provide a dental prophy cup which minimizes or obviates the above-described shortcomings.

SUMMARY OF THE INVENTION

The present invention relates to a dental prophy cup which comprises a body having front and rear portions. The rear portion is adapted for connection to a drive mechanism for rotating the body about a longitudinal axis. The front portion is formed of an elastic material and includes an annular rim encircling a recessed space. The recessed space is formed by a forwardly facing surface. The rim extends longitudinally forwardly and radially outwardly and includes a flexure region about which the rim flexes rearwardly upon being pressed against a tooth surface so that the forwardly facing surface contacts the tooth surface. The flexure region is defined by a reduced thickness of the rim. The thickness increases from the flexure region to a region of maximum thickness located forwardly of the flexure region. The thickness then diminishes from the region of maximum thickness to the front end of the rim.

The forwardly facing surface preferably includes outer and inner convex surface portions disposed forwardly and rearwardly, respectively, of the flexure region.

Abrasive particles are preferably distributed within the body of the prophy cup. As the base material of the cup breaks down, the abrasive particulars are released.

BRIEF DESCRIPTION OF THE DRAWINGS

The objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS OF THE INVENTION

Figure 1:
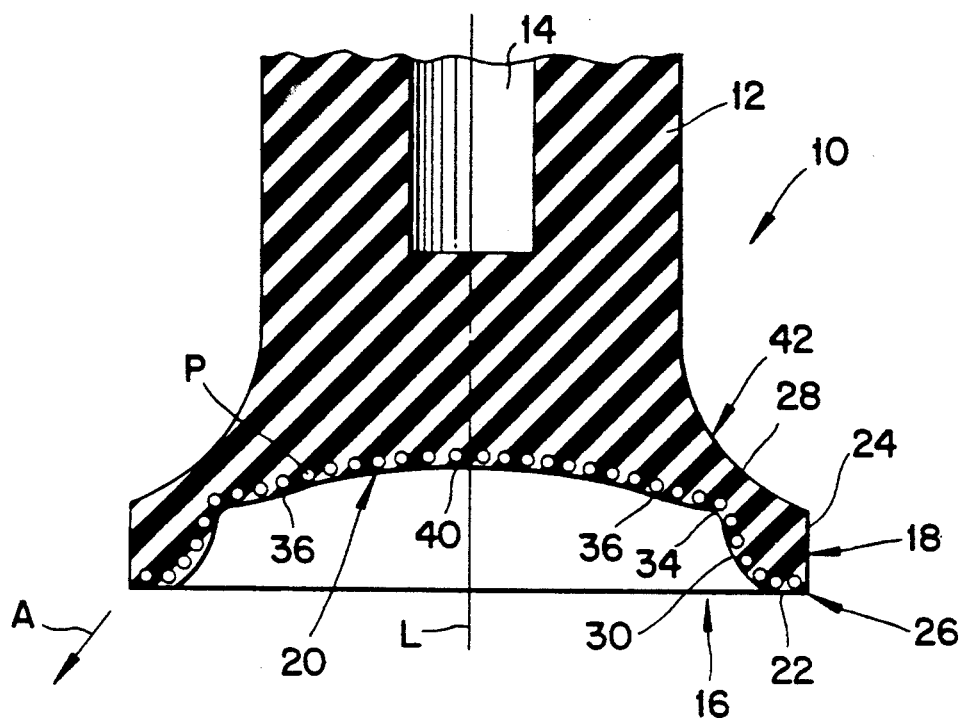
FIG. 1 is a fragmentary longitudinal sectional view taken through a dental prophy cup according to the present invention, with the prophy cup being in a relaxed (unflexed) state.
Figure 2:
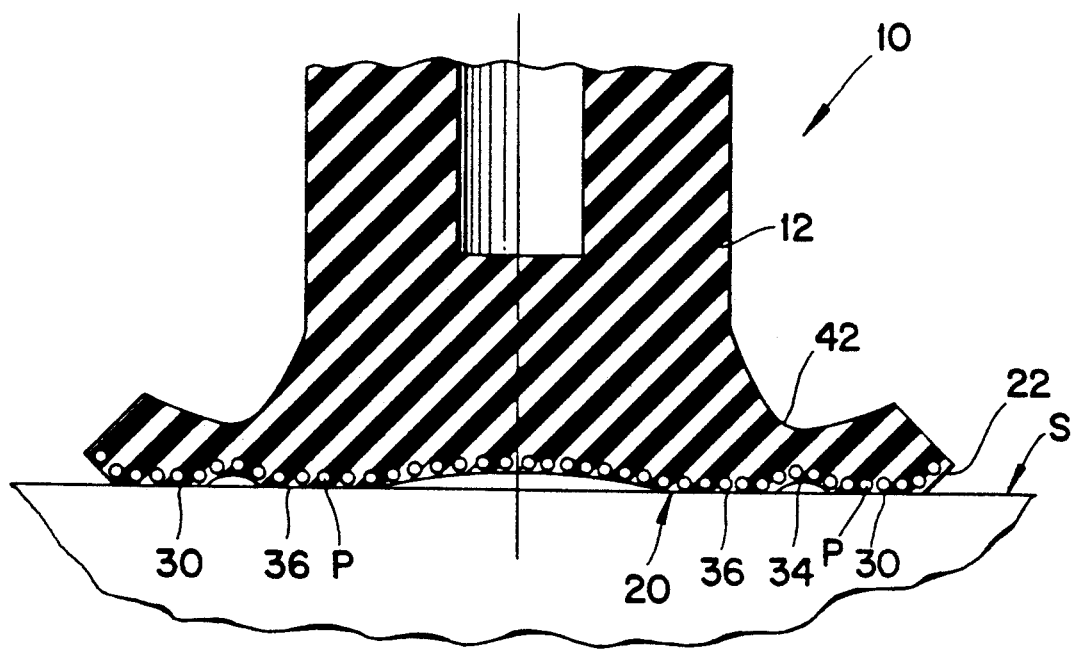
FIG. 2 is a view similar to FIG. 1 after the prophy cup has been flexed upon being pressed against a tooth surface.
Figure 3:
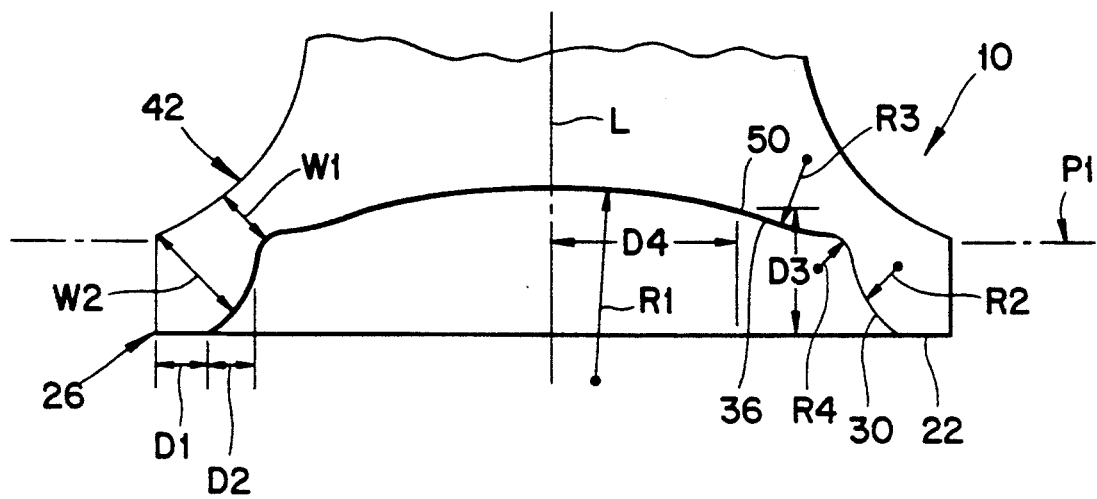
FIG. 3 is a view similar to FIG. 1 depicting various dimensional characteristics of the prophy cup.

A dental prophy cup 10 depicted in FIGS. 1-3 comprises a base portion 12 formed of an elastic material such as silicone. The base portion includes a cavity 14 of non-circular cross section for receiving, e.g., by press fit, a driving mechanism for rotating the body about a longitudinal axis L. The body, which is configured symmetrically about the axis L, also includes a front tooth-engaging end 16 which includes an annular rim 18 and a recessed surface 20.

A forward end of the rim is defined by a radially extending flat surface 22 and an axially extending cylindrical surface 24 which intersect to form a radially outermost edge 26. Extending rearwardly from a rear end of the circumferential surface 24 is an outer concave surface 28.

The recessed surface 20 extends rearwardly from a radially inner end of the radial surface 22. That recessed surface 20 includes an outer convex surface portion 30 which is joined to an inner convex surface portion 32 by a radiused concave bridge surface 34. Extending rearwardly from the inner convex surface portion 36 is a concave surface portion 40 which forms the center of the recessed area 20.

When the cup is unflexed, the rim 18 extends longitudinally forwardly and radially outwardly in direction A. That is, the direction A has longitudinal outward and radially outward components.

The rim 18 includes a flexure region 42 about which the rim can flex when pressed against a tooth. That flexure region 42 is characterized by a minimum reduced cross sectional width W1 (see FIG. 3) formed in part by the bridge surface portion 34, which promotes flexure. The width W1 constitutes a minimum thickness of the flexure region (as is evident from FIG. 3), and intersects the bridge surface portion 34 to form therewith an imaginary line lying in a plane P1 oriented perpendicular to the longitudinal axis L. The cross-sectional width then increases in a direction toward the front end of the rim to a maximum width W2. Then, the cross-sectional width diminishes and eventually terminates at the edge 26. As a result of such a structure, the rim is able to easily flex and flatten out in order to enable the surfaces 30, 36 to contact the tooth surface S as shown in FIG. 2, and thereby maximize the contact area between the recessed surface 20 and the tooth in response to the recommended applied force (i.e., 230 grams of applied force). Also, the rim can flex about the flexure region 42 to enable the surface 20 to conform to non-planar shapes of the tooth surface.

Despite its ability to flex easily, the surface 20 of the rim is able to apply an effective pressure against the tooth surface due to the fact that the cross-sectional width of the rim increases from W1 to W2. That is, the portion of the rim backing-up the surface 30 is of sufficient thickness to effectively oppose excessive rearward bending of the rim. The width W2 is preferably at least 25 percent greater than W1.

Moreover, since the cross-sectional width decreases to form an edge 26, the rim is able to reach subgingival.

The surfaces portions 30 and 36 are, as noted earlier, convex in configuration. As a result, it is ensured that those surfaces, when deformed against a tooth surface, will exhibit a firm, surface-to-surface contact with the tooth surface and will effectively hug the tooth surface as it rides thereacross to apply an effective abrasive cleaning action. In practice, the cup will seldom engage a perfectly flat tooth surface. However, the rim can easily flex about the flexure region 42 to conform to the shape of curved surfaces. When engaging curved tooth surfaces, it is likely that the center surface portion 40 will also engage the tooth surface.

The abrasive cleaning action is improved by abrasive particles P which are in an embedded state within the base material of the prophy cup. This ensures that there will always be an effective amount of abrasive at the tooth surface, despite the presence of blood, water, saliva, etc., and the centrifugal forces imposed by the cup itself, during a cleaning operation. While various types of abrasive particles could be employed, the abrasive particles preferably comprise silicon carbide, e.g., micronized unasil manufactured by Universal Photonics of Hicksville, N.Y., which is of 9.5 mohs hardness. The size of those particles may range from 10 $\mu m$ to 52 $\mu m$, depending upon the particular cleaning operation. The abrasive particles constitute more than 50 percent of the total cup weight, preferably from 70 to 80 percent, and most preferably about 73 percent. The particles must be situated so as to lie at least along the surface 20, but preferably are distributed throughout the entire cup.

One exemplary cup formula constitutes 20 grams of SE 6740 silicone base, 80 grams SE 73 silicone gum, 275 grams unasil 280 (silicon carbide particles), and 1 gram DBPH-50 catalyst.

The silicone base material has been selected to ensure that the base tends to break down during a cleaning operation, whereby new particles are continuously exposed and released to act as free-floating abrasive particles at the tooth surface. Consequently, it is only necessary for the dental technician to utilize a non-abrasive paste as a lubricant, since the prophy cup itself supplies the necessary abrasive particles.

In that exemplary cup, the width W1 was 0.0177 inch, and the width W2 was 0.0331 inch. The radial dimension D1 of the front surface 22 was 0.0156 inch, and the radial dimension D2 from the radial inner edge of the surface 22 to the bridge surface portion 34 was 0.0156 inch. The axial dimension D3 from the plane of the surface 22 to the junction 50 between surfaces 36 and 40 was 0.040 inch. The radial dimension D4 between the center axis L of the cup and the junction 50 was 0.0578 inch. The radius of curvature R1 of the surface 40 was 0.2694 inch. The radii of curvature R2, R3 of the surface portions 30 and 36 were 0.0338 and 0.2219 inch, respectively. The radius of curvature R4 of the bridge surface portion 34 was 0.0086 inch.

The prophy cup can be manufactured in any suitable way, but preferably by a molding step in which the abrasive particles are mixed into liquified silicone, and then the silicone is allowed to harden in sheet form. A mold is pushed against the sheet under temperature and pressure conditions which cause the silicone to become soft and conform to the shape of the mold. The abrasive particles are thus disposed in an embedded state throughout the silicone body of the prophy cup.

It will be appreciated that during a tooth cleaning operation, an operator inserts a non-abrasive lubricating paste into the prophy cup 10 and applies the cup against the tooth surface S. A standard rotational speed for the cup is 1,500 rpm, and the industry recommended application pressure is 230 grams. Under those conditions, the rim 18 of the cup will flex about the flexure region 42 to assume the flattened-out configuration depicted in FIG. 2. As a result, the tooth surface is contacted by both of the surface portions 30, 36 to effectively distribute the applied pressure relatively evenly across the tooth surface to avoid excessive abrasion of the tooth.

Despite the flexibility of the rim 18, the outer surface portion 30 will firmly contact the tooth surface due to the ample thickness W2 of the rim at that surface portion 30. That is, the rim is of sufficient thickness to avoid excessive flexure of the portion of the rim at which the surface portion 30 is disposed.

The pointed terminal end 26 of the rim ensures that the rim will be able to reach subgingival. The rim edge 26 is of sufficient strength (stiffness) to achieve this, since the outer end of the rim begins to taper at a location spaced outwardly from the flexure region 42 (i.e., the tapering begins at the region of maximum thickness W2 rather than at the flexure region).

Since the bridge surface portion 34 is radiused instead of being sharp, the flexing of the rim will impose smaller internal stresses on the rim, whereby fatigue strength is enhanced. In the event that an excessive amount of pressure is applied by the operator during the cleaning operation (i.e., greater than 230 gram), that pressure will be mainly directed to the radially inner surface portion 36 where the linear speed of the cup is low as compared to the linear speed of the outer surface portion 30. Hence, excessive abrasion of the tooth surface will tend to be avoided.

Due to the convex shape of the surface portions 30, 36, those surface portions, when deformed, will snugly engage the tooth surface over essentially their entire area, i.e., no appreciable gaps or non-contacting regions will be created.

As the cleaning proceeds, the rim can be readily flexed in order to conform to curved tooth surfaces.

It is ensured that a uniform amount of abrasive particles will be applied against the tooth surface during the entire cleaning action, since the abrasive particles are distributed throughout the cup body itself. As the cup body wears away during a cleaning operation, new particles P will break away to act as free floating abrasive particles. Thus, despite the presence of blood, saliva, water, etc., and the application of centrifugal force by the rotating cup, there will always be an adequate quantity of abrasive particles for producing an effective abrasive cleaning action.

Figure 4:
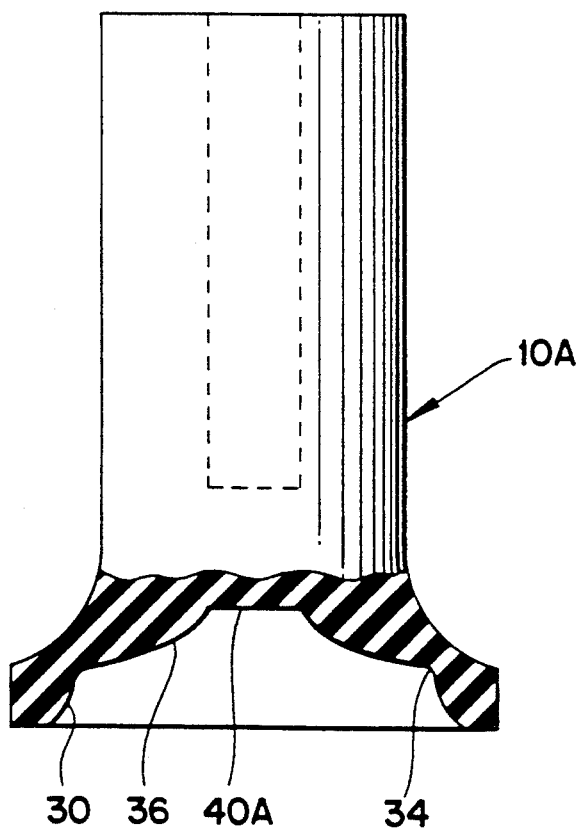
FIG. 4 is a longitudinal sectional view taken through another preferred embodiment of the prophy cup according to the present invention.

It will be appreciated that the center portion 40 of the surface 18 can assume configurations other than that depicted in FIGS. 1-3, for example as shown in FIG. 4 wherein the center surface portion 40A of prophy cup 10A is flat and located farther axially rearwardly than the surface 40.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

I claim:

1. A dental prophy cup comprising a body including front and rear portions, said rear portion adapted for connection to a drive mechanism for rotating said body about a longitudinal axis, said front portion being formed of an elastic material and including an annular rim encircling a recessed space, said recessed space being formed by a forwardly facing surface, said rim extending longitudinally forwardly and radially outwardly and including a flexure region about which said rim flexes rearwardly upon being pressed against a tooth surface so that said forwardly facing surface contacts the tooth surface, said flexure region defined by a reduced thickness of said rim, said rim increasing in thickness from a minimum thickness of said flexure region to a region of maximum thickness located forwardly of said flexure region, said rim diminishing in thickness from said region of maximum thickness to said front end of said rim, said minimum thickness of said flexure region extending annularly about said rim and intersecting said forwardly facing surface at a plane and said plane being oriented perpendicular to said longitudinal axis.

2. A dental prophy cup according to claim 1 wherein said maximum thickness is at least fifty percent greater than said minimum thickness.

3. A dental prophy cup according to claim 1, wherein said forwardly facing surface includes outer and inner surface portions disposed forwardly and rearwardly, respectively, of said plane.

4. A dental prophy cup according to claim 3, wherein said outer surface portion is of convex configuration.

5. A dental prophy cup according to claim 4, wherein said inner surface portion is of convex configuration.

6. A dental prophy cup according to claim 4 including abrasive particles embedded within said body along said forwardly facing surface.

7. A dental prophy cup according to claim 3, wherein said inner surface portion is of convex configuration.

8. A dental prophy cup according to claim 3, wherein said outer and inner surface portions are joined by a radiused bridge surface portion located at said flexure region.

9. A dental prophy cup according to claim 1, wherein said rim includes a forwardly facing surface portion encircling said recessed space.

10. A dental prophy cup according to claim 9, wherein said rim includes a cylindrical surface portion intersecting said forwardly facing surface portion to form a radially outer edge of said rim.

11. A dental prophy cup according to claim 1 including abrasive particles distributed within said body.

12. A dental prophy cup according to claim 11, wherein said particles are formed of silicon carbide.

13. A dental prophy cup according to claim 12, wherein said body is formed of silicone.

14. A dental prophy cup comprising a body including front and rear portions, said rear portion adapted for connection to a drive mechanism for rotating said body about a longitudinal axis, said front portion being formed of an elastic material and including an annular rim encircling a recessed space, said recessed space being formed by a forwardly facing surface, said rim extending longitudinally forwardly and radially outwardly and including a flexure region about which said rim flexes rearwardly upon being pressed against a tooth surface so that said forwardly facing surface contacts the tooth surface, said flexure region defined by a reduced thickness of said rim, said thickness increasing from said flexure region to a region of maximum thickness located forwardly of said flexure region, said rim diminishing in thickness from said region of maximum thickness to said front end of said rim, wherein said forwardly facing surface includes convexly shaped outer and inner surface portions disposed forwardly and rearwardly, respectively, of said flexure region, said outer and inner surfaces being joined by a radiused bridge surface portion situated at said flexure region, a front end of said rim including a flat forwardly facing surface portion encircling said recessed space, abrasive particles distributed within said body.

15. A dental prophy cup comprising a body including front and rear portions, said rear portion adapted for connection to a drive mechanism for rotating said body about a longitudinal axis, said front portion being formed of an elastic material and including an annular rim encircling a recessed space, said recessed space being formed by a forwardly facing surface, said rim extending longitudinally forwardly and radially outwardly and including a reduced thickness portion defining a flexure region about which said rim flexes rearwardly upon being pressed against a tooth surface so that said forwardly facing surface contacts the tooth surface, said flexure region having a minimum extending annularly about said rim and intersecting said forwardly facing surface at a plane and said plane being oriented perpendicularly to said longitudinal axis, said forwardly facing surface including convex outer and inner surface portions disposed forwardly and rearwardly, respectively, of said plane.

16. A dental prophy cup according to claim 15 including abrasive particles distributed within said body.

17. A dental prophy cup according to claim 16, wherein said outer and inner surface portions are joined by a radiused bridge surface portion disposed at said flexure region.

* * * * *